United States Patent
Tsouri

(10) Patent No.: US 10,905,339 B2
(45) Date of Patent: Feb. 2, 2021

(54) OPPORTUNISTIC PLETHYSMOGRAPHY USING VIDEO CAMERAS

(71) Applicant: Gill R. Tsouri, Rochester, NY (US)

(72) Inventor: Gill R. Tsouri, Rochester, NY (US)

(73) Assignee: Rochester Institute of Technology, Rochester, NY (US)

( * ) Notice: Subject to any disclaimer, the term of this patent is extended or adjusted under 35 U.S.C. 154(b) by 68 days.

(21) Appl. No.: 16/270,704

(22) Filed: Feb. 8, 2019

(65) Prior Publication Data
US 2019/0239762 A1    Aug. 8, 2019

Related U.S. Application Data

(60) Provisional application No. 62/627,935, filed on Feb. 8, 2018.

(51) Int. Cl.
| | |
|---|---|
| A61B 5/024 | (2006.01) |
| A61B 5/00 | (2006.01) |
| A61B 5/1171 | (2016.01) |
| H04N 5/232 | (2006.01) |

(52) U.S. Cl.
CPC ........ *A61B 5/02427* (2013.01); *A61B 5/0022* (2013.01); *A61B 5/0077* (2013.01); *A61B 5/02405* (2013.01); *A61B 5/02438* (2013.01); *A61B 5/1176* (2013.01);
(Continued)

(58) Field of Classification Search
CPC . A61B 5/02427; A61B 5/0022; A61B 5/0077; A61B 5/02405; A61B 5/02438; A61B 5/1176; A61B 5/6898; A61B 5/7425
See application file for complete search history.

(56) References Cited

U.S. PATENT DOCUMENTS

| | | |
|---|---|---|
| 8,320,644 B2 | 11/2012 | Singer et al. |
| 8,617,081 B2 | 12/2013 | Mestha et al. |
| 8,768,438 B2 | 7/2014 | Mestha et al. |

(Continued)

OTHER PUBLICATIONS

Poh, Ming-Zher "Non-contact, automated cardiac pulse measurements using video imaging and bling source separation" Optics Express 2010 (Year: 2010).*

(Continued)

*Primary Examiner* — Kim Y Vu
*Assistant Examiner* — Molly Delaney
(74) *Attorney, Agent, or Firm* — Bond, Schoeneck & King, PLLC; Joseph Noto

(57) ABSTRACT

A method for capturing a high-quality cardiac plethysmography signal automatically and seamlessly using the video cameras embedded in personal electronic devices, includes a program running in the background that periodically takes a picture of the person using the device, runs face detection and/or recognition algorithm, and upon detection of a face, records a video, and then processes the video using algorithms to assess video quality by extracting video quality parameters. When video quality parameters are above predefined thresholds, the recorded video is processed further to generate a plethysmography signal indicative of cardiac activity. The plethysmography signal may then be processed to deduce cardiac activity. The method maintains a pleasurable user experience with the personal electronic devices.

36 Claims, 7 Drawing Sheets

(52) U.S. Cl.
CPC .......... *A61B 5/6898* (2013.01); *A61B 5/7425* (2013.01); *H04N 5/23219* (2013.01); *A61B 5/7221* (2013.01)

(56) References Cited

U.S. PATENT DOCUMENTS

| | | | |
|---|---|---|---|
| 8,897,522 | B2 | 11/2014 | Mestha et al. |
| 8,977,347 | B2 | 3/2015 | Mestha et al. |
| 9,336,594 | B2 | 5/2016 | Kyal et al. |
| 9,408,576 | B2 | 8/2016 | Chon et al. |
| 9,615,749 | B2 | 4/2017 | Clifton et al. |
| 2011/0251493 | A1* | 10/2011 | Poh .................. G06K 9/624 600/477 |
| 2012/0081392 | A1 | 4/2012 | Arthur |
| 2012/0190947 | A1 | 7/2012 | Chon et al. |
| 2013/0345568 | A1 | 12/2013 | Mestha et al. |
| 2014/0276118 | A1 | 9/2014 | Tsouri et al. |
| 2015/0131879 | A1 | 5/2015 | Lu et al. |
| 2015/0272456 | A1* | 10/2015 | Kyal .................. A61B 5/0082 600/479 |
| 2015/0313502 | A1* | 11/2015 | Mestha .............. A61B 5/02007 600/473 |
| 2016/0095524 | A1 | 4/2016 | Estepp et al. |
| 2016/0343135 | A1* | 11/2016 | De Haan ............ G06K 9/4652 |
| 2017/0238842 | A1* | 8/2017 | Jacquel .................. A61B 5/743 |

OTHER PUBLICATIONS

Kwon, Sungjun "Validation of heart rate extraction using video imaging on built-in camera system of a smartphone" IEE EMBS 2012. (Year: 2012).*

Tsouri et al. "On the benefits of alternative color spaces for non contact heart rate measurements using standard redgreen-blue cameras". Journal of Biomedical Optics 20(40),048002. Apr. 2015. pp. 1-7.

International Search Report Form PCT/ISA/220, International Application No. PCT/US2019/017174 dated May 3, 2019.

* cited by examiner

OPPORTUNISTIC PLETHYSMOGRAPHY USING VIDEO CAMERAS

CROSS REFERENCE

This application claims the benefit of the filing date of U.S. Provisional Patent Application Ser. No. 62/627,935 filed Feb. 8, 2018, which is hereby incorporated by reference in its entirety.

This invention was made with government support under grant number RO1HL137617 awarded by DHHS National Institutes of Health. The government has certain rights in this invention.

FIELD

The disclosure relates to a method for capturing a cardiac plethysmography signal automatically and seamlessly from a user of a personal electronic device, and in particular capturing the signal through a personal electronic device having a front facing video camera, while maintaining a pleasurable user experience with the electronic device.

BACKGROUND

Accurate measurement of cardiac pulse is essential to a wide variety of clinical applications related to patient diagnosis and monitoring. Examples of such an application are the assessment of Heart Rate, Heart Rate Variability (HRV) and identification of irregular cardiac activity. HRV serves as a quantitative marker of autonomic activity based on the oscillation in the interval between consecutive instantaneous heartbeats, a.k.a., Inter Beat Intervals (IBIs). IBIs are typically detected using the RR intervals extracted from ElectroCardioGraphic (ECG) signals. IBIs are used to compute HRV indicators such as the Standard Deviation of Normal to Normal (SDNN) IBIs, and the Root Mean Square of Successive Differences (RMSSD) between consecutive normal IBIs. In general, these HRV measurements rely on body surface ECG. Nevertheless, PhotoPlethysmoGraphy (PPG) is also used for this purpose as it offers a non-invasive low-cost measurement of cardiac pulse based on blood volume changes in the tissue. The PPG signal can be used for clinical physiological monitoring, offering information regarding blood oxygen saturation, heart rate, blood pressure, and cardiac output. Furthermore, the blood volume pulsations can be correlated to heartbeats enabling a beat-to-beat analysis of cardiovascular activity, thus providing the Mb needed to assess HRV and the hemodynamic response to detect irregular cardiac activity.

Past efforts have demonstrated the feasibility of using VideoPlethysmoGraphic (VPG) signals extracted from facial videos as an alternative to conventional PPG sensors. The major motivation for replacing PPG with VPG is to provide seamless non-contact monitoring to improve on patient comfort and avoid the use of dedicated sensors. VPG provides very weak cardiac signals compared to those obtained with contact based sensors. Despite this limitation, VPG has been successfully used in the past under controlled environments, i.e., scenarios where the lighting source, position of subject with relation to camera, and subject motion are known and set in advance. More specifically, VPG works well when the subject is very still, faces the camera directly and the light in the background is adequately strong and unchanging over time.

The major challenge in VPG today is to enable this technology beyond the controlled environment of a lab and into the varying and often unpredictable environments of everyday life. More specifically, the challenge to make VPG work while a subject is moving, and the lighting source is varying and unknown. Overcoming this challenge would enable VPG to work on mobile smart devices, such as smartphones and tablets that have an embedded camera facing the user. It is well established that use of such devices is widespread and increasing. The average person over 50 years old spends 2-5 hours a day in front of a tablet and/or smartphone providing ample opportunity to capture VPG signals. All past work to address this challenge relied on the use of solutions and algorithms from the field of video and image processing, including motion compensation algorithms and cancellation of varying illuminating light. Due to the weak cardiac signals provided with VPG (very low SNR signal), these solutions do not provide adequate performance.

A major disadvantage of the prior art is the high complexity of implementation associated with elaborate algorithms used for motion compensation and ambient light compensation that must be applied to the entire frame pixels. The art currently lacks a completely different approach than trying to correct for motion and ambient light to capture a cardiac signal. The art lacks a monitoring process that frees the user from participating in the monitoring process to overcome low patient compliance which is one of the major impediments to home-based telemedicine.

SUMMARY

In accordance with one aspect of the present disclosure, there is provided a method for capturing high-quality cardiac plethysmography signals automatically and seamlessly, including:

providing a personal electronic device containing a video camera embedded therein and a computer program running in the background that periodically takes a picture of the person using the device, runs at least one of a face detection and face recognition algorithm, and upon detection of a face, records a video, and then processes the video using algorithms which assess video quality by extracting video quality parameters;

processing the recorded video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device.

In accordance with another aspect of the present disclosure, there is provided a method for capturing high-quality cardiac plethysmography signals automatically and seamlessly, including:

providing a personal electronic device containing a video camera embedded therein and a computer program running in the background that periodically takes a picture of the person using the device, runs at least one of a face detection and face recognition algorithm, and upon detection of a face, recording a video with automated video capture functions on, freezing the automated video capture functions upon stabilization of the automated video capture functions, and recording with the automated video capture functions off, and then processes the video using algorithms which assess video quality by extracting video quality parameters;

processing the recorded video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device.

These and other aspects of the present disclosure will become apparent upon a review of the following detailed description and the claims appended thereto.

DETAILED DESCRIPTION

Figure 1:
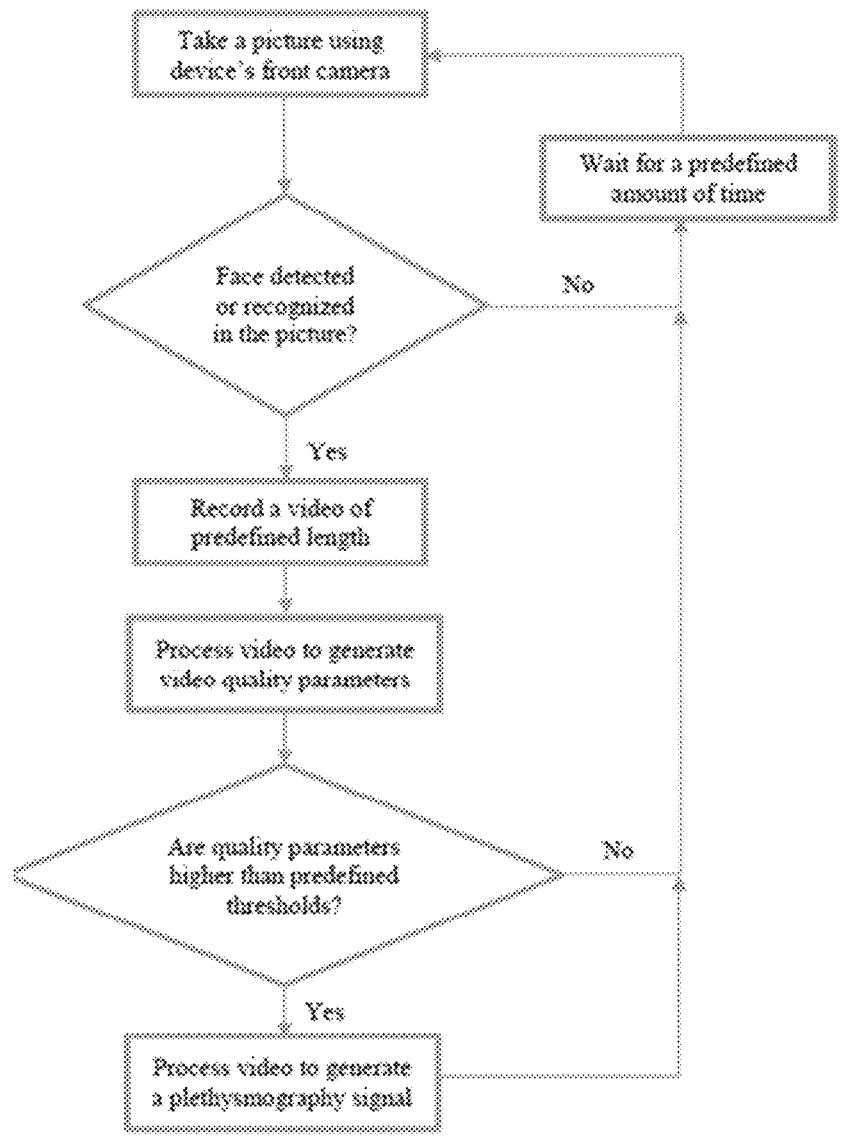
FIG. 1 is a flowchart showing a method for passively capturing a cardiac plethysmography signal automatically and seamlessly in accordance with an embodiment of the present disclosure.

The disclosure is directed to a process for capturing a high-quality cardiac plethysmography signal automatically and seamlessly using the video cameras embedded in personal electronic devices, such as smartphones, tablets and laptops. The process uses a program running in the background that periodically takes a picture of the person using the device, runs face detection and/or recognition algorithm, and upon detection of a face, records a video, and then processes the video using algorithms to assess video quality by extracting video quality parameters. When video quality parameters are above predefined thresholds, the recorded video is processed further to generate a plethysmography signal indicative of cardiac activity. The plethysmography signal may then be processed to deduce cardiac activity, such as resting heart rate and arrhythmias. The process maintains a pleasurable user experience with the personal electronic devices.

Instead of trying to correct for motion and ambient light, the disclosure opportunistically captures a cardiac signal when conditions are favorable using the appropriate video quality parameters. Given the amount of time a typical user spends in front of a device with an embedded camera, this generates enough data to offer clinical significance. In an embodiment, recording a video includes initiating a recording with automated video capture functions turned on. Suitable automated video capture functions include auto focus, auto gain and white balancing functions. Once the auto functions have stabilized, i.e., the picture is in focus and the intensity is at a predetermined level, the automated video capture functions would be frozen to ensure the auto functions do not interfere with the extraction of the cardiac signal. Recording is then continued. The recording of a video with the auto function frozen would commence for a typical duration of 20 seconds. Optionally, the video length can be longer or shorter depending on the cardiac function being monitored. For example, when extracting average heart rate a video of 3 seconds is sufficient but can be made longer to improve accuracy. In another example, when extracting heart rate variability a video length of at least 20 seconds is typically recorded.

An advantage of the disclosure is in providing a feasible solution for seamlessly monitoring cardiac activity in the background while the user uses the device. This is due to the low complexity of implementation associated with the calculation of video quality parameters applied to average R G B, compared to elaborate algorithms used for motion compensation and ambient light compensation that must be applied in prior art processes. Monitoring in the background frees the user from participating in the monitoring process. The present disclosure overcomes low patient compliance which is one of the major impediments to home-based telemedicine.

In an embodiment, a method for capturing a high-quality cardiac plethysmography signal automatically and seamlessly, includes providing a personal electronic device, such as smartphones, tablets and laptops, containing a front facing video camera embedded therein and a computer program running in the background that periodically takes a picture of the person using the device; running a face detection and/or recognition algorithm; and upon detection of a face freezing automated video capture functions such as auto-gain, white-balance and auto-focus; recording a video; and then processing the video using algorithms designed to assess video quality by extracting video quality parameters assessing degree of motion of the detected and/or recognized face, spectral signature from detected facial region, face detection consistency and face recognition dissimilarity; when the video quality parameters are above predefined thresholds, processing the recorded video further to generate a plethysmography signal indicative of cardiac activity; and optionally, processing the plethysmography signal to deduce cardiac activity, such as resting heart rate and arrhythmias. The method maintains a pleasurable user experience with the personal electronic devices. The method is passive with respect to the user.

In an embodiment, a method for capturing high-quality cardiac plethysmography signals automatically and seamlessly, includes providing a personal electronic device, such as smartphone, tablet and laptop, containing a video camera embedded therein and a computer program running in the background that periodically takes a picture of the person using the device, running a face detection and/or recognition algorithm, and upon detection of a face, recording a video, and then processing the video using algorithms designed to assess video quality by extracting video quality parameters; when the video quality parameters are above predefined thresholds, the recorded video is processed further to generate a plethysmography signal indicative of cardiac activity; and optionally, processing the plethysmography signal to deduce cardiac activity, such as resting heart rate and arrhythmias. The method maintains a pleasurable user experience with the personal electronic devices.

A pleasurable user experience means that the user is not required to participate in the process of recording the video, e.g., the user is not required to initiate the recording and once recording begins, the user is not required to hold still and/or place his face within a rectangle drawn on the screen. A pleasurable user experience also means that the video recording and subsequent processing of recorded video does not impair or diminish the device's capabilities to perform tasks initiated by the user to an extend noticeable by the user. In this context, device capabilities include battery life, real-time processing speed, video display on the screen when watching a movie, etc.

Video quality parameters include:

Motion—the center of the detected facial region is calculated across frames in the video, the average central location across the frames is calculated, and then the average deviation of the centers across the frames from the average central location is quantified. The average deviation (Davg) is optionally processed further to obtain the following metric:

$$M = \frac{2*10^9 - Davg}{2*10^9}.$$

If M is smaller than the threshold 0.5, the video is not processed to extract a cardiac signal.

Spectral signature—the average Red, Green and Blue pixel values are calculated within the detected facial region in each frame to provide a sequence of 3 values across all frames. The average values per frame are converted to Hue to provide a single sequence of numbers across frames. Spectral estimation is then performed over the sequence to provide a spectrum. The frequencies with the highest spectral peak are identified and quantified with respect to their prominence compared to the other spectral peaks. Optionally, the spectral power components within a window of 0.01 Hz around the spectral peak in the spectrum are summed, the result is divided by the sum of all the spectral power components in the spectrum. If the result is smaller than the threshold 0.1, the video is not processed to extract a cardiac signal.

Face detection consistency—a ratio is calculated between the frames in the video where a face is detected and the total number of frames in the video. Optionally, the number of video frames with a detected face is divided by the total number of frames in the video. If the result is smaller than the threshold 0.9, the video is not processed to extract a cardiac signal. Optionally, face recognition can be used on top of face detection consistency. A dissimilarity metric is calculated by comparing the face detected in a frame with a registered photo of a specific user. If the dissimilarity metric is smaller than the threshold 1, the video is not processed to extract a cardiac signal.

Figure 2:
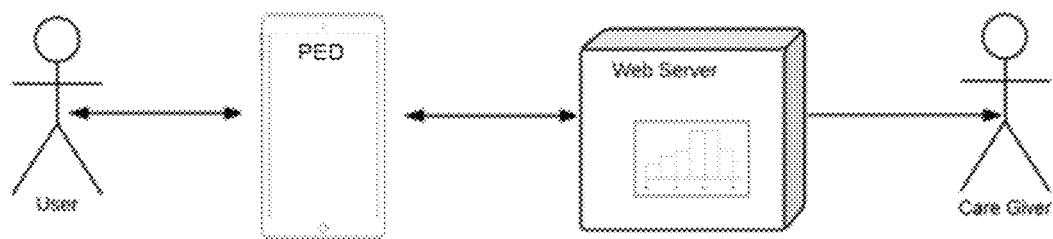
FIG. 2 is a schematic depicting access of the user data by a care giver in accordance with an embodiment of the present disclosure.

In an embodiment, the cardiac signal extracted can be used as follows:

At the server, the average heart rate (HR) and the Heart Rate Variability (HRV) are calculated for every video that passed the quality parameters thresholds. The HR is stored in a database using an entry that contains: [User ID, Date of Measurement, Time of Measurement, HR measurement, HRV measurement, Quality Parameters]. The database can be accessible via the web through secure login and a dashboard can be used to present the data. As shown in FIG. 2, this data can be accessed by a care giver to help track the user's health status over time, track the user's compliance with taking medication, identify changing smoking habits, etc. The data can also be accessed by the user or by a physician finding the average HR and/or diary useful for providing care.

Figure 3:
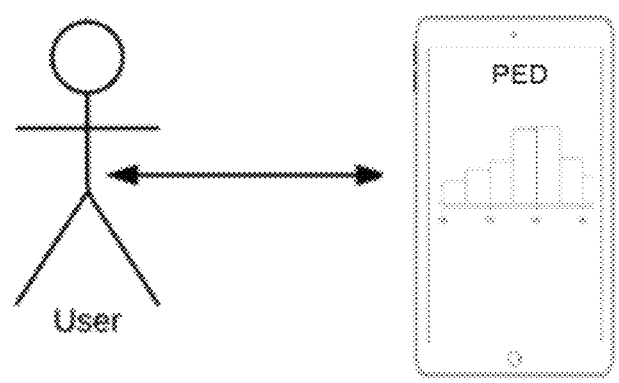
FIG. 3 is a schematic depicting implementation of the entire process on the PED in accordance with an embodiment of the present disclosure.
Figure 4:
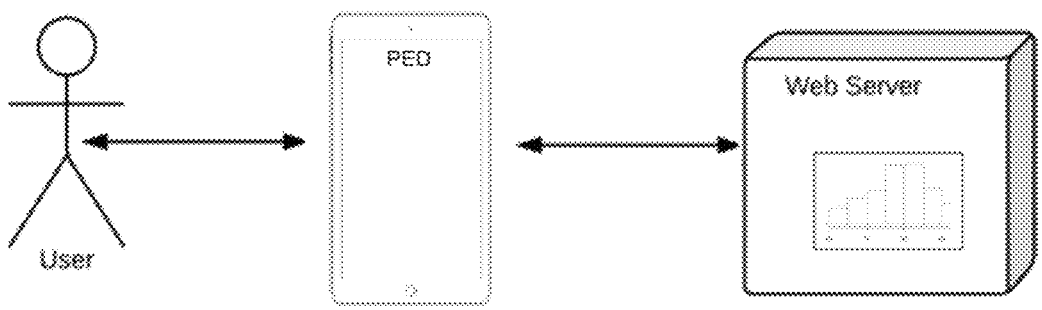
FIG. 4 is a schematic depicting implementation of a portion of the process on the PED and the remainder of the process in a cloud server in accordance with an embodiment of the present disclosure.

In an embodiment, the entire process may be implemented on the device, as shown in FIG. 3. In another embodiment, as shown in FIG. 4, part of the process may be implemented on the device and the rest in a cloud server to which data is uploaded from the device. Any embodiment of the disclosure may be reduced to practice in the form of a downloadable APP or a program embedded in the device prior to deployment.

Figure 5:
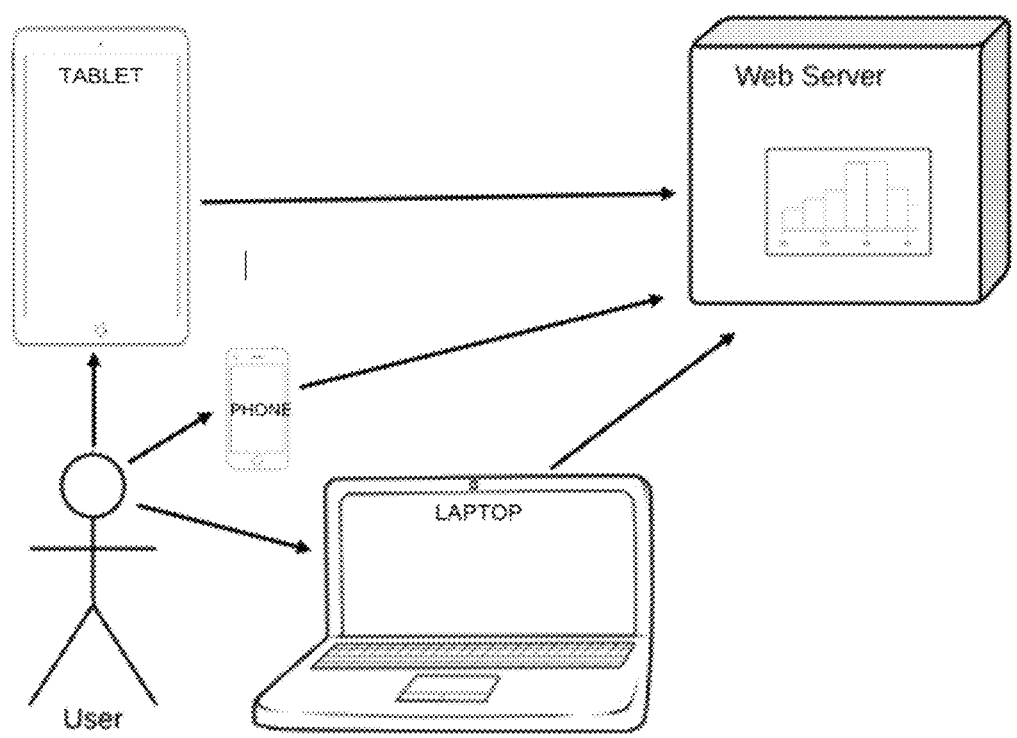
FIG. 5 is a schematic depicting implementation of the process across multiple devices to gather signals from the same user in accordance with an embodiment of the present disclosure.

In an embodiment, the process may be used across multiple devices to gather signals from the same person. For example, FIG. 5 illustrates an APP may be installed by a user on a smartphone, a tablet and a laptop and signals extracted from all devices may be aggregated at a remote server to form data of that user.

An example of an embodiment of the process uses an Android APP for Android smartphones and tablets that runs part of the described process as a service program running in the background while the user seamlessly uses the device. The APP then uses cloud services to send processed data to continue the process at a remove server. The APP and server follow the flow chart shown in FIG. 1, as described in the steps below.

Process steps implemented on the APP installed on the device:

1) Run a process program that periodically takes a picture (e.g., every 2 min.) using the front camera and uses a face detection function to detect a face in the image.

2) If no face is detected go back to Step 1.

3) If a face is detected, activate camera's auto-focus and auto-gain functions for a period of time to stabilize the auto functions, e.g., for 5 seconds, lock all camera auto functions and record a video, e.g., for 20 sec., using, e.g., 30 frames per second.

4) The recorded video is processes as follows:

a) Apply face detection algorithm to every $15^{th}$ frame in the video. Store in memory the four coordinates corresponding to the four corners of a rectangle around the detected face for all frames where a face was detected. For frames with no detected face, store 4 zeros as coordinates.

b) Derive an "average rectangle" with four coordinates that are the averages of each corresponding coordinate across the rectangles of all detected frames.

c) For every frame in the video, calculate and store in memory the average Red Green and Blue values within the average rectangle. This results in three numbers per frame.

d) For every frame in the video, calculate and store in memory the average Red Green and Blue values outside the average rectangle. This results in three numbers per frame.

e) Save files to a designated folder on the device with the following data: rectangle coordinates corresponding to detected faces in frames, coordinates of average rectangle, average Red Green Blue numbers calculated for all frames, and start time of video capture.

5) Synchronize the files on the designated tablet folder with a cloud server folder (e.g., copy files from tablet folder to a remote server using the internet).

6) Go back to Step 1.

Process steps implemented on the remote server:

7) Wait for new files to be uploaded to the server.

8) When new files from a video recording reach the server, generate the following video quality parameters:

a) Face Detection Parameter: calculate the ratio between the number of frames without rectangle coordinates of zero and the total number of frames.

b) Motion Parameter: calculate the center of the detected facial region is calculated across frames in the video, the average central location across the frames is calculated, and then the average deviation of the centers across the frames from the average central location is quantified. The average deviation (Davg) is optionally processed further to obtain the following metric:

$$M = \frac{2*10^9 - Davg}{2*10^9}.$$

c) Spectral Signature Parameter: Calculate the average Red Green and Blue pixel values within the detected facial region in each frame to provide a sequence of 3 values across all frames. Convert the average values per frame to Hue to provide a single sequence of numbers across frames. Perform spectral estimation over said sequence to provide a spectrum. Sum the spectral power components within a window of 0.01 Hz around the spectral peak in the spectrum and divide the result by the sum of all the spectral power components in the spectrum.

9) If the Face Detection Parameter is above 0.9 and the Motion Parameter is higher than 0.5 and the Spectral Signature Parameter is higher than 0.1 go to Step 10, otherwise go back to Step 7.

10) Generate a plethysmography signal Hue (H) across frames using the average Red (R), Green (G) and Blue (B) numbers as follows:

$$H' = \begin{cases} 0, \text{ if } C = 0 \\ \frac{G-B}{C} \mod 6, \text{ if } M = R \\ \frac{B-R}{C} + 2, \text{ if } M = G \\ \frac{R-G}{C} + 4, \text{ if } M = G \end{cases} ; H = 60 \deg \times H'$$

where M=max(R,G,B), m min(R,G,B) and C=M−m.

11) Apply known signal processing algorithms to clean H', including filtering, de-trending, normalizing, and the like.

12) Go back to Step.

Current commercially available solutions for cardiac screening and monitoring require the subject being monitored to use a dedicated sensor that needs to be purchased at a considerable cost and used properly by the user or a healthcare professional. The disclosure enables to perform cardiac monitoring and screening at very low cost, without relying on dedicated sensors and without requiring participation from the user. The widespread use of smart devices with cameras coupled with the use of an easily downloadable APP to implement the disclosed process enables many applications of telemedicine currently unavailable using existing technologies.

For example, the disclosure can be used to detect and track Atrial Fibrillation (AF), an ailment affecting over 3M people in the US. It can also be used to screen for arrhythmias in asymptomatic patients belonging to high risk groups that would otherwise go unattended.

Another possible use is in medical surveys performed over the internet; a questionnaire may be accompanies with measurement of cardiac activity. As a specific example, one may consider to track heart rate variability as a measure of vagal tone activity in response to a stress-inducing questionnaire typically used to assess regulation of stress.

Another example is in using the technology in the Emergency Department (ED) where patients typically wait for very long periods of time without being attended. Monitoring their heart rate can provide warning of deterioration in health. Currently, such patients are not being monitored due to limited manpower in EDs.

The disclosure could help law enforcement agencies when questioning suspects in airports and elsewhere by detecting elevated heart rate in response to questioning.

The disclosure can be used to infer customer interest while shopping online based on elevated heart rate. This can help online retailers such as Amazon to better target products to potential customers.

The disclosure can be implemented on the operating system of smart devices such as iOS and Android so that video monitoring of health becomes an integral part of the device. This would augment existing healthcare packages provided by companies such as Apple and Samsung.

The disclosure will be further illustrated with reference to the following specific examples. It is understood that these examples are given by way of illustration and are not meant to limit the disclosure or the claims to follow.

Example 1—Diary of Resting Heart Rate (HR)

The disclosed process for capturing cardiac signals is used further to implement a HR diary. A subject installs the aforementioned Android APP on a smartphone. The APP sends data to a remote server where it is further analyzed.

Figure 6:
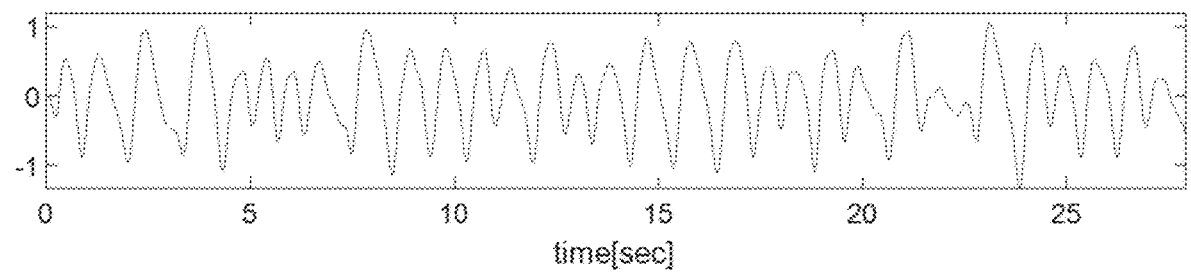
FIG. 6 depicts a typical cardiac signal extracted with Hue using the method in accordance with an embodiment of the present disclosure.

FIG. 6 depicts a typical cardiac signal extracted using the aforementioned process with Hue: At the server, the average heart rate (HR) is calculated for every video data coming in from the smartphone. The HR is then stored in a database using an entry that contains: [User ID, Date of Measurement, Time of Measurement, HR measurement, Quality Parameters].

Figure 7:
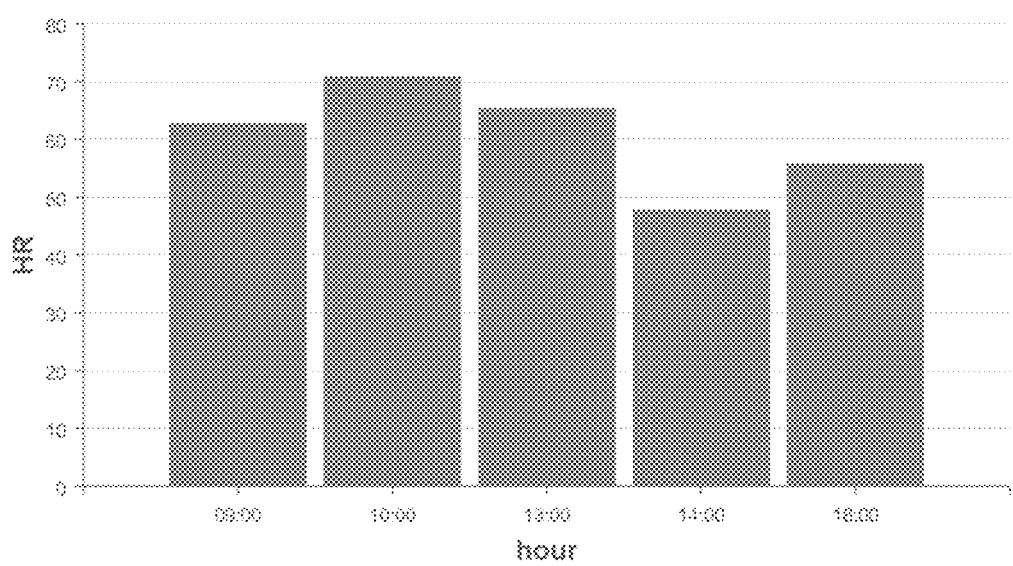
FIG. 7 shows a snapshot of a typical dashboard in accordance with an embodiment of the present disclosure.

The database is accessible via the web through secure login and a dashboard is used to present the data on the screen. The snapshot shown in FIG. 7 presents a typical dashboard.

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for capturing high-quality cardiac plethysmography signals automatically and seamlessly, comprising:

providing a personal electronic device containing a video camera embedded therein and a computer program running in the background that periodically takes a picture of the person using the device with automated video capture functions on, runs at least one of a face detection and face recognition algorithm, and upon detection of a face freezes the automated video capture functions upon stabilization of the automated video capture functions, records a video with the automated video capture functions off, and then processes the video using algorithms which assess video quality by extracting video quality parameters;

processing the recorded video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device.

2. The method of claim 1, wherein the automated video capture functions comprise auto-gain, white-balance or auto-focus.

3. The method of claim 1, wherein the personal electronic device comprises a smartphone, tablet or laptop.

4. The method of claim 1, wherein the video camera comprises a front facing video camera.

5. The method of claim 1, wherein the video quality parameters comprise degree of motion of a detected or recognized face, spectral signature from a detected facial region, and face detection consistency.

6. The method of claim 1, wherein the cardiac activity comprises average heart rate, heart rate variability or arrhythmias.

7. The method of claim 5, wherein the degree of motion of the detected or recognized face is assessed by calculating the center of a detected facial region across frames in the video, calculating the average central location across the frames, and then quantifying the average deviation of the centers across the frames from the average central location.

8. The method of claim 5, wherein the spectral signature is assessed by calculating the average Red, Green and Blue pixel values within a detected facial region in each frame to provide a sequence of 3 values across all frames, converting the average values per frame to Hue to provide a single sequence of numbers across frames, performing a spectral estimation over the sequence to provide a spectrum, identifying the frequencies with the highest spectral peak, and quantifying the identified frequencies prominence compared to the other spectral peaks.

9. The method of claim 5, wherein the face detection consistency is assessed by calculating the ratio between the frames in the video where a face is detected to the total number of frames in the video.

10. The method of claim 1, wherein the deduced cardiac activity comprises:

calculating the average heart rate (HR) and the Heart Rate Variability (HRV) for every video that exceeds the quality parameter threshold;

storing the HR in a database using an entry that comprises User ID, Date of Measurement, Time of Measurement, HR measurement, HRV measurement, and Quality Parameters; and displaying the database.

11. The method of claim 1, wherein the entire method is implemented on the personal electronic device.

12. The method of claim 1, wherein a portion of the method is implemented on the personal electronic device and the remaining portion of the method is implemented in a cloud server to which data is uploaded from the device.

13. The method of claim 1, wherein the method is reduced to practice in the form of a downloadable APP or a program embedded in the device prior to deployment.

14. The method of claim 1, wherein the method is implemented across multiple devices to gather signals from the same person.

15. The method of claim 1, wherein an APP is installed by a user on a smartphone, a tablet and a laptop and signals extracted from all devices are aggregated at a remote server to form data of that user.

16. A method for capturing high-quality cardiac plethysmography signals automatically and seamlessly, comprising:

providing a personal electronic device containing a video camera embedded therein and a computer program running in the background that periodically takes a picture of the person using the device, runs at least one of a face detection and face recognition algorithm, and upon detection of a face, records a video, and then processes the video using algorithms which assess video quality by extracting video quality parameters which comprise degree of motion of a detected or recognized face, spectral signature from a detected facial region, and face detection consistency;

processing the recorded video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device.

17. The method of claim 16, wherein the degree of motion of the detected or recognized face is assessed by calculating the center of a detected facial region across frames in the video, calculating the average central location across the frames, and then quantifying the average deviation of the centers across the frames from the average central location.

18. The method of claim 16, wherein the spectral signature is assessed by calculating the average Red, Green and Blue pixel values within a detected facial region in each frame to provide a sequence of 3 values across all frames, converting the average values per frame to Hue to provide a single sequence of numbers across frames, performing a spectral estimation over the sequence to provide a spectrum, identifying the frequencies with the highest spectral peak, and quantifying the identified frequencies prominence compared to the other spectral peaks.

19. The method of claim 16, wherein the face detection consistency is assessed by calculating the ratio between the frames in the video where a face is detected to the total number of frames in the video.

20. A method for capturing high-quality cardiac plethysmography signals automatically and seamlessly, comprising:

providing a personal electronic device containing a video camera embedded therein and a computer program running in the background that periodically takes a picture of the person using the device, runs at least one of a face detection and face recognition algorithm, and upon detection of a face, records a video, and then processes the video using algorithms which assess video quality by extracting video quality parameters;

processing the recorded video further when the video quality parameters are above predefined thresholds, to generate a plethysmography signal indicative of cardiac activity; and optionally, processing the plethysmography signal to deduce cardiac activity, wherein the deduced cardiac activity comprises:

calculating the average heart rate (HR) and the Heart Rate Variability (HRV) for every video that exceeds the quality parameter threshold;

storing the HR in a database using an entry that comprises User ID, Date of Measurement, Time of Measurement, HR measurement, HRV measurement, and Quality Parameters; and displaying the database, wherein the method maintains a pleasurable user experience with the personal electronic device.

21. A method for capturing high-quality cardiac plethysmography signals automatically and seamlessly, comprising:

providing a personal electronic device containing a video camera embedded therein and a computer program running in the background that periodically takes a picture of the person using the device, runs at least one of a face detection and face recognition algorithm, and upon detection of a face, records a video, and then processes the video using algorithms which assess video quality by extracting video quality parameters;

processing the recorded video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device, wherein a portion of the method is implemented on the personal electronic device and the remaining portion of the method is implemented in a cloud server to which data is uploaded from the device.

22. A method for capturing high-quality cardiac plethysmography signals automatically and seamlessly, comprising:

providing a personal electronic device containing a video camera embedded therein and a computer program running in the background that periodically takes a picture of the person using the device with automated video capture functions on, runs at least one of a face detection and face recognition algorithm, and upon detection of a face freezes the automated video capture functions upon stabilization of the automated video capture functions, and processes a video with the automated video capture functions off using algorithms which assess video quality by extracting video quality parameters;

processing the video further when the video quality parameters are above predefined thresholds, to generate a plethysmography signal indicative of cardiac activity; and optionally, processing the plethysmography signal to deduce cardiac activity, wherein the method maintains a pleasurable user experience with the personal electronic device.

23. The method of claim 22, wherein the automated video capture functions comprise auto-gain, white-balance or auto-focus.

24. The method of claim 22, wherein the personal electronic device comprises a smartphone, tablet or laptop.

25. The method of claim 22, wherein the video camera comprises a front facing video camera.

26. The method of claim 22, wherein the video quality parameters comprise degree of motion of a detected or recognized face, spectral signature from a detected facial region, and face detection consistency.

27. The method of claim 22, wherein the cardiac activity comprises average heart rate, heart rate variability or arrhythmias.

28. The method of claim 26, wherein the degree of motion of the detected or recognized face is assessed by calculating the center of a detected facial region across frames in the video, calculating the average central location across the frames, and then quantifying the average deviation of the centers across the frames from the average central location.

29. The method of claim 26, wherein the spectral signature is assessed by calculating the average Red, Green and Blue pixel values within a detected facial region in each frame to provide a sequence of 3 values across all frames, converting the average values per frame to Hue to provide a single sequence of numbers across frames, performing a spectral estimation over the sequence to provide a spectrum, identifying the frequencies with the highest spectral peak, and quantifying the identified frequencies prominence compared to the other spectral peaks.

30. The method of claim 26, wherein the face detection consistency is assessed by calculating the ratio between the frames in the video where a face is detected to the total number of frames in the video.

31. The method of claim 22, wherein the deduced cardiac activity comprises:

calculating the average heart rate (HR) and the Heart Rate Variability (HRV) for every video that exceeds the quality parameter threshold;

storing the HR in a database using an entry that comprises User ID, Date of Measurement, Time of Measurement, HR measurement, HRV measurement, and Quality Parameters; and displaying the database.

32. The method of claim 22, wherein the entire method is implemented on the personal electronic device.

33. The method of claim 22, wherein a portion of the method is implemented on the personal electronic device and the remaining portion of the method is implemented in a cloud server to which data is uploaded from the device.

34. The method of claim 22, wherein the method is reduced to practice in the form of a downloadable APP or a program embedded in the device prior to deployment.

35. The method of claim 22, wherein the method is implemented across multiple devices to gather signals from the same person.

36. The method of claim 22, wherein an APP is installed by a user on a smartphone, a tablet and a laptop and signals extracted from all devices are aggregated at a remote server to form data of that user.

* * * * *